United States Patent
Guo et al.

(10) Patent No.: US 10,034,853 B2
(45) Date of Patent: Jul. 31, 2018

(54) PPAR α/γ DUAL AGONIST AND ITS APPLICATION

(71) Applicant: Shanghai University of Traditional Chinese Medicine, Shanghai (CN)

(72) Inventors: Fujiang Guo, Shanghai (CN); Cheng Huang, Shanghai (CN); Li Feng, Shanghai (CN); Yiming Li, Shanghai (CN)

(73) Assignee: Shanghai University of Traditional Chinese Medicine, Shanghai (CN)

( * ) Notice: Subject to any disclaimer, the term of this patent is extended or adjusted under 35 U.S.C. 154(b) by 0 days.

(21) Appl. No.: 14/784,606

(22) PCT Filed: Apr. 15, 2014

(86) PCT No.: PCT/CN2014/075354
§ 371 (c)(1),
(2) Date: Oct. 15, 2015

(87) PCT Pub. No.: WO2014/169800
PCT Pub. Date: Oct. 23, 2014

(65) Prior Publication Data
US 2016/0074358 A1  Mar. 17, 2016

(30) Foreign Application Priority Data
Apr. 16, 2013  (CN) .......................... 2013 1 0130440

(51) Int. Cl.
*A61K 31/353* (2006.01)
*A23L 33/10* (2016.01)
*C07D 311/32* (2006.01)

(52) U.S. Cl.
CPC ............ *A61K 31/353* (2013.01); *A23L 33/10* (2016.08); *C07D 311/32* (2013.01); *A23V 2002/00* (2013.01)

(58) Field of Classification Search
CPC ..... A61K 31/353; A23L 33/10; C07D 311/32; A23V 2002/00
See application file for complete search history.

(56) References Cited

U.S. PATENT DOCUMENTS

2003/0035851 A1*  2/2003  Chen .................... A61K 31/352
424/728

OTHER PUBLICATIONS

Harwood, L.M.,"An improved procedure for cyclisation of chalcones to flavanones using celite supported potassium fluoride in methanol: total synthesis of bavachinin." Synthetic Communications 20.5 (1990): 649-657.*
Bhalla, V. K., "Some new flavonoids from Psoralea corylifolia." Tetrahedron Letters 9.20 (1968): 2401-2406.*
Hu, L.,"Prodrugs: effective solutions for solubility, permeability and targeting challenges." IDrugs 7.8 (2004): 736-742.*
Kuntz, S.,"Comparative analysis of the effects of flavonoids on proliferation, cytotoxicity, and apoptosis in human colon cancer cell lines." European journal of nutrition 38.3 (1999): 133-142.*
Shekunov, B.,"Crystallization processes in pharmaceutical technology and drug delivery design." Journal of crystal growth 211.1 (2000): 122-136.*
Book, Gold. "Compendium of Chemical Terminology." International Union of Pure and Applied Chemistry (2014); excerpt p. 528; p. 1-2.*
Serajuddin, A.T.M., "Salt formation to improve drug solubility." Advanced drug delivery reviews 59.7 (2007): 603-616.*

* cited by examiner

*Primary Examiner* — John M Mauro
(74) *Attorney, Agent, or Firm* — Ware, Fressola, Maguire & Barber LLP

(57) ABSTRACT

The present invention discloses a PPAR α/γ dual agonist and its application. The PPAR α/γ dual agonist comprises an effective amount of the compounds represented by formula I or/and its pharmaceutically acceptable derivative. Wherein, $R_1$ is selected from alkoxyl or ester group; $R_2$ is selected from hydroxyl or ester group. The PPAR α/γ dual agonist according to the present invention can be used for preparing drugs and functional foods for preventing or/and treating metabolic syndrome, especially glucose or/and lipid disorders, with extensive and bright prospects of application.

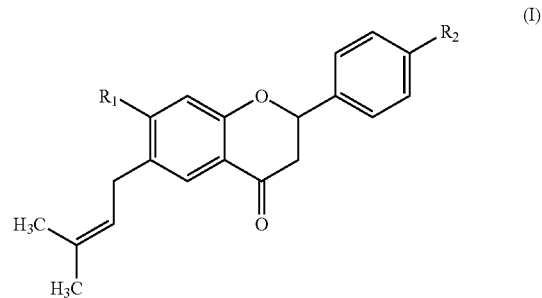

3 Claims, 3 Drawing Sheets

PPAR α/γ DUAL AGONIST AND ITS APPLICATION

TECHNICAL FIELD

The present invention relates to a PPAR α/γ dual agonist and its application, belonging to the technical field of medicines.

BACKGROUND OF THE INVENTION

Metabolic syndrome is a common disease characterized by glucose disorders and dyslipidemia, accompanied by elevated LDL-c levels and reduced HDL-c levels. Metabolic syndrome mainly includes obesity, diabetes, hyperlipidemia and atherosclerosis, wherein the diabetic patients are also often complicated with hyperlipidemia, cardiovascular disease, diabetic nephropathy, diabetic neuropathy and other diseases.

World Health Organization has reported that more than 220 million people are suffering from diabetes worldwide. China has become the country with world's highest number of diabetic patients. According to the data of research report published on "The New England Journal of Medicine" on Mar. 25, 2010, there have been more than 92 million diabetic patients in China. Incidence and growth rate of diabetes are significantly increasing now. It is estimated that China has 150 million pre-diabetics currently. Continued expansion of the diabetic population has brought enormous economic and medical burden to the society. World Health Organization has pointed out that heart disease, stroke and diabetes will bring at least $550 billion losses in economic to China in next 10 years if no effective measures are taken to contain the development of these diseases.

It has been shown that pharmacological activations of peroxisome proliferator-activated receptors (PPARs) are effective therapeutic approaches to correct some aspects of metabolic syndrome mainly hyperlipidemia and type II diabetes mellitus. PPARs belong to the superfamily of nuclear hormone receptors that function as ligand-inducible transcription factors modulating the expression of target genes, which include three subtypes PPAR α, PPAR β/δ and PPAR γ (Feige J N, Gelman L, Michalik L, Desvergne B, & Wahli W (2006) From molecular action to physiological outputs: peroxisome proliferator-activated receptors at nuclear receptors at the crossroads of key cellular functions. *Progress in lipid research* 45(2):120-159.). PPARs can not only regulate glucose homeostasis, lipid metabolism, and inflammation, but also accommodate obesity, cell differentiation and cancer (Desvergne B & Wahli W (1999) Peroxisome proliferator-activated receptors: nuclear control of metabolism. *Endocrine reviews* 20(5): 649-688; Moraes L A, Piqueras L, & Bishop-Bailey D (2006) Peroxisome proliferator-activated receptors and inflammation. *Pharmacology & therapeutics* 110(3): 371-385.).

Specific lipid-lowering drug fibrates have been used in the treatment of dyslipidemia via a PPAR α-dependent activating mechanism (Issemann I, Prince R A, Tugwood J D, & Green S (1993) The peroxisome proliferator-activated receptor: retinoid X receptor heterodimer is activated by fatty acids and fibrate hypolipidaemic drugs. *Journal of molecular endocrinology* 11(1): 37-47.). PPAR γ agonist thiazolidinediones (TZDs), such as rosiglitazone (ROS) and pioglitazone on the market now, are very effective in improving glycemic management (Lehmann J M, et al. (1995) An antidiabetic thiazolidinedione is a high affinity ligand for peroxisome proliferator-activated receptor gamma (PPAR gamma). *The Journal of biological chemistry* 270(22): 12953-12956.). Dual PPAR α/γ agonists may provide enhanced therapeutic value for the treatment for complicated metabolic syndrome. A lot of pharmaceutical and clinical trials have investigated the collective effects of dual PPAR α/γ agonists on sustained glucose, lipid and inflammation control (Staels B & Fruchart J C (2005) Therapeutic roles of peroxisome proliferator-activated receptor agonists. *Diabetes* 54(8): 2460-2470.). Despite their excellent potencies, dual agonists, including ragaglitazar, MK-0767, muraglitazar and aleglitazar, have been withdrawn from clinical studies because of obvious adverse effects (Nissen S E, Wolski K, & Topol E J (2005) Effect of muraglitazar on death and major adverse cardiovascular events in patients with type 2 diabetes mellitus. *JAMA: the journal of the American Medical Association* 294(20): 2581-2586.). Thus, development of novel, effective and safer dual PPAR α/γ agonist is urgently needed.

SUMMARY OF THE INVENTION

For problems and needs described above, the object of the present invention is to provide a PPAR α/γ dual agonist and its application, and to screen a new kind of drugs for the prevention or/and treatment of metabolic diseases.

A PPAR α/γ dual agonist according to the present invention comprises an effective amount of the compounds represented by formula I or/and its pharmaceutically acceptable derivatives:

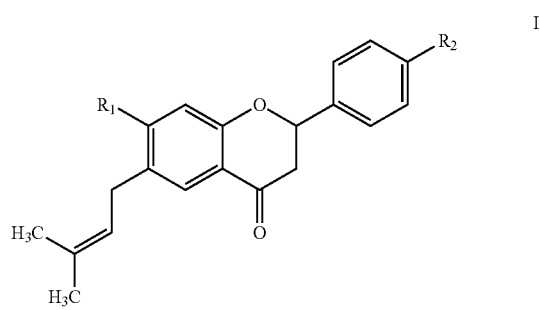

wherein:
R$_1$ is selected from alkoxyl or ester group; R$_2$ is selected from hydroxyl or ester group.

In some embodiments, the R$_1$ is selected from alkoxyl, the R$_2$ is selected from hydroxyl or ester group.

In some embodiments, the R$_1$ is selected from C$_1$-C$_4$ alkoxyls, the R$_2$ is selected from hydroxyl or C$_1$-C$_4$ ester groups.

In some embodiments, the R$_1$ is selected from methoxyl or ethoxyl, the R$_2$ is selected from hydroxyl or methoxycarbonyl or ethoxycarbonyl.

In some embodiments, both R$_1$ and R$_2$ are selected from ester group.

In some embodiments, both R$_1$ and R$_2$ are selected from C$_1$-C$_4$ ester groups.

In some embodiments, both R$_1$ and R$_2$ are selected from methoxycarbonyl or ethoxycarbonyl.

The pharmaceutically acceptable derivatives according to the present invention are preferably pharmaceutically acceptable salts or solvates.

The pharmaceutically acceptable salts can be the addition salts formed by compounds showed in Formula I and an acid or base; the pharmaceutically acceptable solvates can be the solvates formed by of the compounds showed in Formula I and water or alcohol solvents.

The compounds showed in Formula I according to the present invention can be derived from a natural extract or chemical synthesis.

The PPAR α/γ dual agonist according to the present invention can be used for preparing drugs and functional foods for preventing or/and treating metabolic syndrome, especially glucose or/and lipid disorders (such as: the diseases of obesity, diabetes, hyperlipidemia, atherosclerosis and so on).

As the preferred embodiment, the PPAR α/γ dual agonist according to the above-described application is selected from the compounds of the following formula:

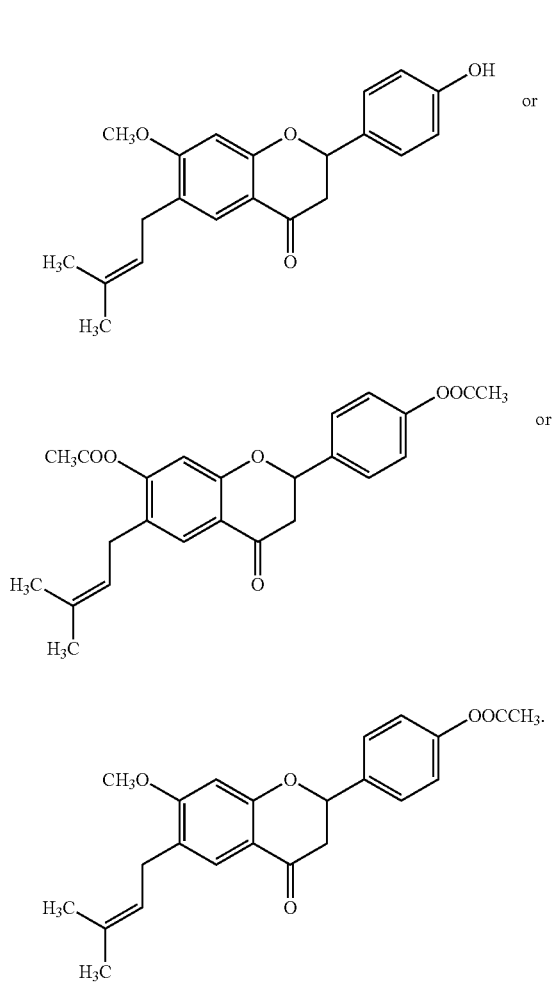

The above-described compound A (the English name is bavachinin) can be isolated from the seeds of *Psoralea corylifolia*, compound B can be prepared by the bavachin acylation reaction, compound C can be prepared by the acylation reaction of compound A.

According to this present invention, the drugs can be administered to patients with various routes, including, but not limited to oral, transdermal, intramuscular, subcutaneous and intravenous medication administration.

Experiments showed that the compounds of formula I according to the present invention can significantly increase transcriptional activities and mRNA levels of the target genes of PPAR-α and -γ, and can be treated as the potent dual PPAR α/γ agonist. In addition, to further verify the in vivo effects of the compounds of formula I, the present invention studied the blood glucose and lipid parameters of db/db mice and diet-induced obese (dio) mice. The mice experiment results indicated that the compounds of formula I can effectively reduce blood glucose levels, and alleviate blood glucose tolerance and lipid disorders in db/db mice as the dual PPAR α/γ agonist. Thus, the compounds of formula I can be used to prepare drugs and functional foods for preventing or/and treating metabolic syndrome, especially glucose or/and lipid disorders, with extensive and bright prospects of application.

SPECIFIC EMBODIMENTS

Figure 1:
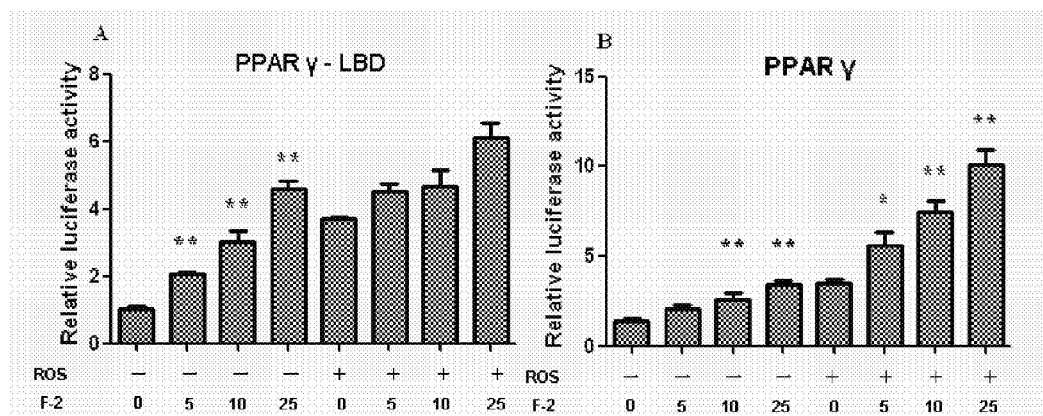
FIG. 1 shows the effects of bavachinin (compound A, labeled as F-2) on the PPAR-γ transcriptional activity.

The further detailed descriptions of the present invention are made combing the drawings and specific embodiments as below.

Example 1: The Preparation of Bavachinin (Compound A)

10.0 kg of the seeds of *Psoralea corylifolia* L. (Legminosae) were extracted three times (2 hours each) under reflux in 95 vol % ethanol (80 L). The solvent was evaporated under reduced pressure to yield crude extract (about 800 mL). The crude extract was suspended in water (800 mL), then partitioned with petroleum ether (1000 mL×3) and ethyl acetate (1000 mL×3) successively. The fraction of ethyl acetate were combined, concentrated under reduced pressure and chromatographed with a silica gel column, eluting with a gradient of the petroleum ether and ethyl acetate (10:1-1:5, V/V); the collected components were subjected to silica gel column again with cyclohexane and acetone as gradient elution (9:1-1:1, V/V) firstly, then reverse phase column chromatography with methanol—water gradient (60 vol % methanol-80 vol % methanol), at last Sephadex LH-20 (methanol) was used to purify, and bavachinin was obtained as white powder.

$^1$H-NMR (CDCl$_3$, 400 MHz) δ: 1.70 (3H, s, CH$_3$-5"), 1.74 (3H, s, CH$_3$-4"), 2.78 (1H, dd, J=2.8, 16.8 Hz, H-3), 3.04 (1H, dd, J=13.2, 16.8 Hz, H-3), 3.24 (2H, d, J=7.2 Hz, H-1"), 3.85 (3H, s, OCH$_3$), 5.27 (1H, m, H-2"), 5.38 (1H, dd, J=2.8, 13.2 Hz, H-2), 6.45 (1H, s, H-8), 7.34 (2H, d, J=8.4 Hz, H-3', 5'), 6.90 (2H, d, J=8.4 Hz, H-2', 6'), 7.68 (1H, s, H-5);

$^{13}$C-NMR (CDCl$_3$, 100 MHz) δ: 18.0 (C-5"), 26.1 (C-4"), 28.0 (C-1'), 44.4 (C-3), 56.0 (7-OCH$_3$), 79.8 (C-2), 98.8 (C-8), 114.1 (C-10), 115.9 (C-3', 5'), 121.9 (C-2"), 125.2

(C-6), 127.3 (C-5), 128.2 (C-2', 6'), 131.1 (C-1'), 133.3 (C-3"), 156.3 (C-4'), 162.5 (C-9), 164.4 (C-7), 191.5 (C-4); ESI-MS: (Pos. mode) [M+H]$^+$ 339.

The above data of the analytical results are consistent with that reported in the literature (Biol Pharm Bull. 2005, 28(12): 2253-2257.).

Example 2: The Preparation of Compound B 20 mg bavachin [also isolated from the seeds of *Psoralea corylifolia*, the purify method can be found in the literature Bioorg Med Chem 2004, 12: 4387-4392.] was dissolved in 1 mL of pyridine, then with 1 mL of acetic anhydride added, placed under room temperature for 24 hours, then 10 mL ethyl acetate solvent was added, using water to back-extract, the organic phase was collected, concentrated, and chromatographed by Sephadex LH-20 column to obtain compound B as white powder.

$^1$H-NMR (CDCl$_3$, 400 MHz) δ: 1.72 (3H, s, CH$_3$-5"), 1.77 (3H, s, CH$_3$-4"), 2.34 (6H, s, 2×CH$_3$CO), 2.88 (1H, dd, J=2.8, 16.8 Hz, H-3), 3.06 (1H, dd, J=13.2, 16.8 Hz, H-3), 3.23 (2H, d, J=7.2 Hz, H-1"), 5.22 (1H, m, H-2"), 5.49 (1H, dd, J=2.8, 13.2 Hz, H-2), 6.80 (1H, s, H-8), 7.18 (2H, d, J=8.4 Hz, H-3', 5'), 7.51 (2H, d, J=8.4 Hz, H-2', 6'), 7.82 (1H, s, H-5).

Example 3: The Preparation of Compound C 20 mg bavachinin [compound A] was dissolved in 1 mL of pyridine, with 1 mL of acetic anhydride added, placed under room temperature for 24 hours, then 10 mL ethyl acetate solvent was added, using water to back-extract, the organic phase was collected, concentrated, and chromatographed by Sephadex LH-20 column to obtain compound C as white powder.

$^1$H-NMR (CDCl$_3$, 400 MHz) δ: 1.72 (3H, s, CH$_3$-5"), 1.76 (3H, s, CH$_3$-4"), 2.35 (3H, s, CH$_3$CO), 2.83 (1H, dd, J=2.8, 16.8 Hz, H-3), 3.04 (1H, dd, J=13.2, 16.8 Hz, H-3), 3.27 (2H, d, J=7.2 Hz, H-1"), 3.88 (3H, s, OCH$_3$), 5.29 (1H, m, H-2"), 5.47 (1H, dd, J=2.8, 13.2 Hz, H-2), 6.47 (1H, s, H-8), 7.18 (2H, d, J=8.4 Hz, H-3', 5'), 7.52 (2H, d, J=8.4 Hz, H-2', 6'), 7.70 (1H, s, H-5).

Example 4: Using Dual-Luciferase Reporter Gene Assay to Analyze the Effects of the Compounds A, B and C on the Transcriptional Activities of PPAR γ and PPAR α

Reporter gene assay was used to detect the impacts of the compounds A, B and C on the transcriptional activities of PPAR γ and PPAR α. The inventors used the PPAR-α, α-LBD, γ and γ-LBD plasmids to detect the impacts of bavachinin on transcription activities of these two PPAR subtype. All the transfections were added to 293T cells (ATCC) overnight and then removed. The positive agonists or the test compounds were diluted in fresh media, and then added into the cells. After incubating for another 24 hours, the cells were harvested to detect luciferase activity.

(1) 293T Cell Culture 293T cells were cultured in Dulbecco's modified Eagle's medium (DMEM) with 10% fetal bovine serum and 1% Penicillin/Streptomycin anti-DMEM high glucose medium at 37° C. and 5% CO$_2$. 293T cells in log phase were seeded into 48-well plate with the cell density of 1×10$^5$~2×10$^5$ cells/mL.

(2) Plasmids for Transfection pCMX-Gal-mPPAR γ LBD plasmids, Gal4 reporter vector MH100×4-TK-Luc recombinant plasmids and renilla luciferase internal reference plasmids; PPAR α-LBD plasmids; PPAR γ plasmids; PPAR α plasmids.

The plasmid construction can be referenced as following: Biochemical and Biophysical Research Communications 2006(348): 571-578; Cell Metabolism. 2(2005) 239-249; J. Biol. Chem. 272 (1997) 18779-1878; Cell 83 (1995) 803-812.

(3) Transfection

When the cells grew to a density of 50 to 80% after seeded in plate overnight, it's good to carry out the transfection. All the transfections, which included 10 μg of total plasmids and 15 μL FuGENE-HD transfection reagent per mL of DMEM, were placed at room temperature for 15 minutes and then added to 293T cells (ATCC) overnight and then removed.

(4) Compounds Intervention

After incubating overnight, the compound A or B or C or positive PPAR γ/α agonists rosiglitazone (as the specific agonistic ligand of PPAR γ) or WY14643 (as the specific agonistic ligand of PPAR α) with different concentrations diluted by complete medium (2, 5, 10, 25, 50 μmol/L) were added into cells. The final concentration of positive agonists was 20 μmol/L).

(5) Cell Collection and Treatment

After 24 hours, cells were washed twice with PBS to remove the remaining cell culture medium; 65 μL lysis buffer was added into each well and oscillated by the shaker for 15 minutes until cell lysis was complete. Finally the cell lysate was transferred into a 1.5 mL centrifuge tube; The cell lysate was centrifuged at 5000 rpm for 5 minutes and then 10 μL supernatant was taken to a new centrifuge tube for testing.

(6) Luciferase Intensity Measurement

We conducted the luciferase reporter assay using Dual-Luciferase Reporter Assay System (Promega, USA). The transfection efficiency was normalized using the internal reference renilla luciferase activity. All transfection experiments were independently repeated for at least three times, with each experimental group having at least two deputy holes.

The Bio-Tek, Synergy HT multifunctional microplate reader was used to detect the fluorescence intensity of firefly and renilla. After normalizing via the internal reference renilla luciferase activity, the relative luciferase activity was expressed by the ratio of the fluorescence intensity of firefly luciferase and renilla luciferase.

(7) Statistical Analysis

Data were expressed as mean±standard error of mean (SEM). One-way ANOVA was used to analyze statistically differences between groups with LSD test for multiple comparisons using SPSS 16.0. The EC$_{50}$ values were calculated using GraphPad Prism 5.0. A P value≤0.05 was regarded as statistically significant different.

(8) Experimental Results

Figure 2:
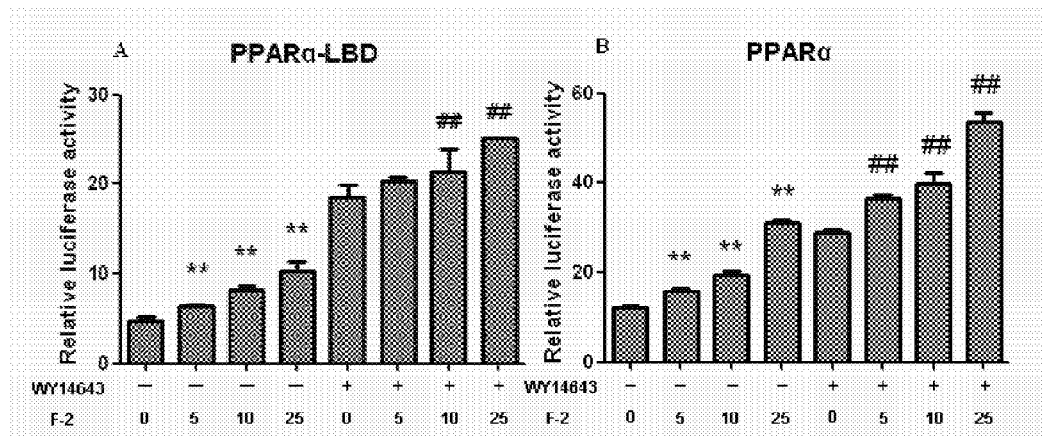
FIG. 2 shows the effects of bavachinin (compound A, labeled as F-2) on the PPAR-α transcriptional activity.

We used reporter assay system to validate the effects of the compounds of formula I on PPAR γ and α transcription activity. The results were shown in FIGS. 1 and 2. We identified that compound A (F-2) can increase PPAR γ-dependent luciferase activity in dose-dependent manner with EC$_{50}$ value of 8.6 μM, whereas its transactivation at 25 μM was nearly equal to PPAR γ agonist rosiglitazone (ROS) at 20 μM (FIG. 1). Compound A was also found to activate the PPAR α isoform at an EC$_{50}$ value of 17.3 μM, indicating more transactivation compared with the PPAR α-specific full agonist WY14643 (FIG. 2). The transcription activities of compounds B and C on two PPAR isoforms were less than that of compound A.

TABLE 1

Effective concentrations (EC$_{50}$ value, μM) of the compounds A, B and C for PPAR α and γ

| No. | EC$_{50}$ (μM) | |
| --- | --- | --- |
|  | PPAR γ | PPAR α |
| compound A | 8.60 | 17.32 |
| compound B | 18.82 | 28.52 |
| compound C | 12.35 | 12.87 |

Table 1 showed that the compounds of formula I exhibited significant transcriptional activities for PPAR α/γ. Thus, the compounds of formula I can be used as the potent dual PPAR α/γ agonists.

Example 5: Effects of the Compounds A, B and C on the Expression Levels of PPAR α/γ Target Genes in HepG2 Cells Used Real-time fluorescence quantitative PCR (Real-time PCR) to detect how the compounds A, B and C regulate the expression of PPAR γ/α-related target genes in liver HepG2 cells.
(1) HepG2 Cell Culture
HepG2 cells was grown in Dulbecco's modified Eagle's medium (DMEM, HyClone) with 10% fetal bovine serum (FBS, HyClone) and 1% Penicillin/Streptomycin (Gibco) at 37° C. and 5% CO$_2$. HepG2 cells at logarithmic growth phase were plated in 12-well plates with the cell density was 5×10$^4$ cells/mL, and then were treated by compound A for 24 hours. Quantitative PCR analysis was performed using β-actin as an endogenous reference.
(2) Dosing Intervention
When the density of HepG2 cells was grown about 60%, compound A (dissolved in DMSO as a stock solution) diluted with complete medium was added into cells. The final concentration was 25 μM (μmol/L).
(3) Total RNA Extraction
After 24 hours, total RNA of treated HepG2 cells was isolated using TRIzol reagent (Takara, Japan) according to the manual.
(4) Synthesis of cDNA
The total RNA was reversely transcribed to cDNA applying the reverse transcription kit (Thermo, Mass., USA). We established 20 μL reverse transcription reaction system according to Table 2. The reaction system was mixed and placed at room temperature (25° C.) for 5 minutes, incubated at 42° C. for 1 hour, incubated at 70° C. for 5 minutes. cDNA was stored at −20° C.

TABLE 2

Reverse transcription reaction system

| Total RNA + Double distilled water | 10 μL |
| --- | --- |
| oligo(dT)$_{18}$primer | 1 μL |
| 5× Reaction buffer | 4 μL |
| Random hexamer primer | 1 μL |
| 10 mM Deoxynucleotide triphosphate mixture (dNTP Mix) | 2 μL |
| RiboLock ™ RNase inhibitor | 1 μL |
| ReverAid ™ M-MuLV Reverse Transcriptase | 1 μL |
| Total volume | 20 μL |

(5) Real-Time PCR
All primers were designed by the Prime 3.0 software. Briefly, after an initial denaturation at 95° C. for 10 minutes, the cDNA was amplified by 40 cycles of PCR (95° C., 15 seconds; 60° C., 60 seconds). All experiments were repeated at least three times independently.

TABLE 3

Real-time PCR reaction system

| Ingredient | volume |
| --- | --- |
| Double distilled water | 2.9 μL |
| SYBRGreen Mix | 5 μL |
| Foword Primer | 1 μL |
| Reverse Primer | 1 μL |
| cDNA | 0.1 μL |
| Total volume | 10 μL |

Figure 3:
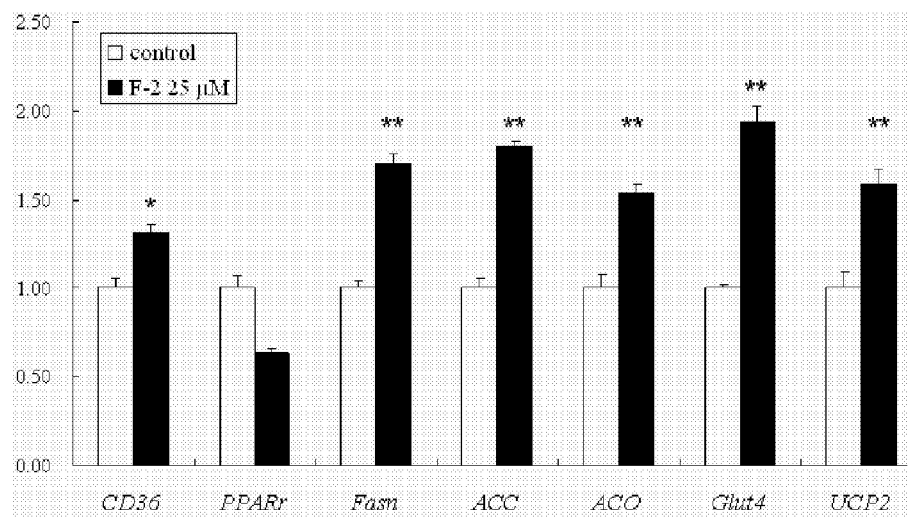
FIG. 3 shows the effects of bavachinin (compound A, labeled as F-2) on the expression of target genes of PPAR α/γ in HepG2 cells.

(6) Experimental Results
The compounds of formula A, B and C significantly increased PPAR α/γ target genes involved in glucose transport and lipid synthase, transport or oxidation with different activity, including solute carrier family 2 (facilitated glucose transporter), member 4 (GLUT4), thrombospondin receptor (CD36), lipoprotein lipase (LPL), fatty acid synthase (Fasn) and acetyl-CoA oxidase (ACO). However, they did not effect PPAR α/γ themselves, which are similar to the positive drug rosiglitazone. FIG. 3 showed the effects of bavachinin (compound A, F-2) on the expression of PPAR α/γ target genes.

Example 6: Compounds A, B and C Improve the Blood Glucose and Glucose Intolerance in db/db Mice The db/db mice were treated with 5 mg/kg/d rosiglitazone or 100 mg/kg/d compound A for 6 days. Mice were fasted 8 hours before subjected to a dose of 1 g glucose per kg body weight. Blood was taken from tail and measured at 0, 15, 30, 60 and 90 minutes. The data were expressed with means±SE, n=9 for each group.
*P<0.05; **P<0.01.
The db/db mice with leptin receptor mutation begin to show the symptoms of obesity, hyperlipidemia, insulin resistance, hyperglycemia and others at 4 weeks. This is an ideal kind of mice model for obese diabetic mice.
The db/db mice were kept in polycarbonate cages under regulated temperature (22-23° C.) and controlled humidity (50%-60%) with 12-hour light/12-hour dark cycle. All the mice were allowed to adapt to the standard housing conditions. Mice and food were weighed regularly to investigate the changes in body weight and food intake.
During the experimental period, the eight-week old db/db mice were treated with water and a normal standard cylindrical diet. Rosiglitazone and compound A, which were dissolved in the vehicle (double distilled water containing 10% DMSO), were administrated intragastricly vehicle, or 5 mg/kg rosiglitazone or 100 mg/kg compound A for 3 weeks. An intraperitoneal glucose tolerance test (IPGTT) was carried out after one week of treatment. Mice were fasted 8 hours before subjected to a dose of 1 g glucose per kg body weight. Blood was taken from tail at 0, 15, 30, 60, and 90 minutes. After 11 days of treatment, 0.75 U/kg body weight of insulin was injected intraperitoneally to perform intraperitoneal insulin tolerance test (IPITT). Blood was taken from tail at 0, 15, 30, 60, 90 and 120 minutes. After 20 days, all the db/db mice were anaesthetized by pentobarbital sodium after 8-hour fast. Blood and tissues were collected and stored at −80° C. for the further analysis.

Experimental Results

After 6 days treatment, compounds A, B and C reduced the fasting blood glucose in db/db mice. Compared with mice treated with vehicle, compound A reduced about 20% glucose, indicating its activity is stronger than rosiglitazone (5%). The activities of compounds B and C were far lower than compound A with reduction about 10% and 8% glucose approximately. Meanwhile the three compounds improved glucose and insulin tolerance in mice with different extent.

Figure 4:
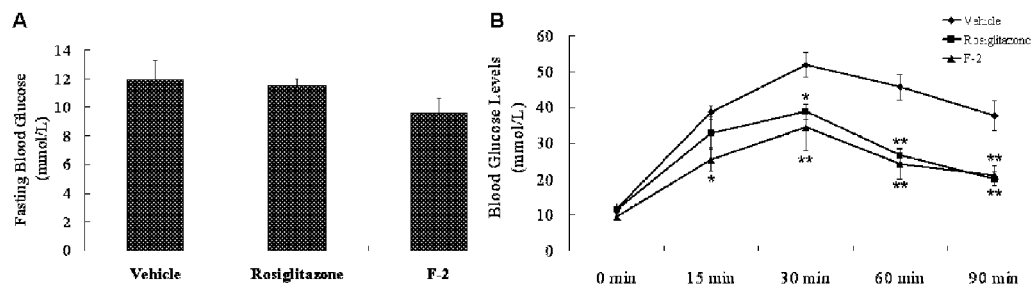
FIG. 4 shows the effects of bavachinin (compound A, labeled as F-2) on blood glucose levels of db/db mice.

The detailed results were illustrated in FIG. 4. FIG. 4A showed the effects of compound A on fasting blood glucose in db/db mice; FIG. 4B indicated compound A improved glucose tolerance (IPGTT) in db/db mice.

Example 7: Compounds A, B and C Induce 3T3-L1 Preadipocyte Differentiation

3T3-L1 fibroblast cell line is widely used for adipocyte differentiation models. After induction by insulin, dexamethasone and PPAR γ agonist, 3T3-L1 can differentiate into typical adipocytes.

For adipocyte differentiation, 3T3-L1 cells were seeded into 12-well plate to full confluence for 2 days and then incubated with completed medium containing 10 μg/mL human insulin (Sigma-Aldrich), 1 μM dexamethasone (Sigma-Aldrich) and the test compounds at 37° C. and 7.5% $CO_2$. After 2 days of induction, the medium was replaced with a maintenance medium (completed medium including 10 μg/mL insulin and the test compounds) for additional 2 days (Day 0-Day 2). Thereafter, the medium was refreshed with fresh medium with the test compounds for 4 days (Day 2-Day 6). The test compounds dissolved in dimethylsulfoxide (DMSO) was diluted by the completed medium (final DMSO concentration, 0.1%) at indicated concentration. rosiglitazone was used as a positive compound.

The 3T3-L1 cells were washed with PBS twice, fixed with 10% formalin at room temperature for 10 minutes and then stained with oil red O (Sigma-Aldrich, St. Louis, Mo.) at 37° C. for 30 minutes. The pictures were taken using an Olympus microscope (Tokyo, Japan).

The Experimental Results

We used insulin, dexamethasone and rosiglitazone or bavachinin to induce 3T3-L1 cell differentiation. During induction, compound A was added into the medium and differentiated adipocytes were observed via oil red o staining after 6 days treatment. At 1 μM, bavachinin induced 3T3-L1 cell differentiation and lipid droplets formation, and adipocytes were almost fully differentiated at 10 μM. FIG. 1D showed that compound A (F-2) was as potent as rosiglitazone on adipocyte differentiation. Although compounds B and C promoted adipocyte differentiation, their activities with a concentration of 25 μM were nearly equal to the activity of compound A at 5 μM.

Figure 5:
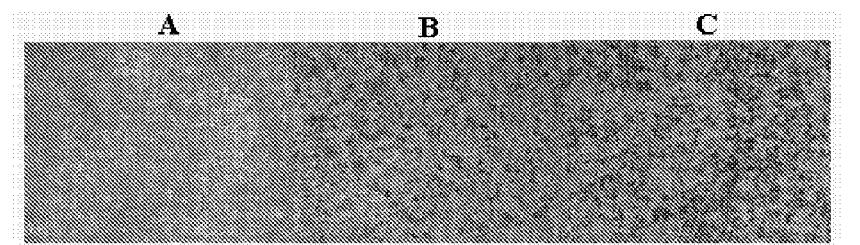
FIG. 5 shows the effects of bavachinin (compound A, labeled as F-2) on 3T3-L1 adipocyte differentiation.

FIG. 5 embodied the impact of bavachinin (compound A, F-2) on adipocyte differentiation of 3T3-L1. FIG. 5A showed 3T3-L1 cells treated with insulin and dexamethasone nearly did not differentiated; FIG. 5B showed 3T3-L1 cells were induced to differentiate into adipocytes after treated with insulin, dexamethasone and 10 μM rosiglitazone; FIG. 5C showed 3T3-L1 was induced to differentiate into adipocytes after treated with insulin, dexamethasone and compound A of 25 μM.

Example 8: Compounds A, B and C Relieve Lipid Disorders in Diet-Induced Obese (dio) Mice For the therapy study, the six-week old female C57BL/6J mice were fed with high-fat diet (HFD, 60% of calories from fat) for 12 weeks to induce obesity and insulin resistance (DIO). The mice were divided into 3 groups according to body weight and fasting blood glucose (n=9, 7, 7, 7). The age-matched lean normal C57BL/6J mice were treated with low-fat diet (LFD, 10% of calories from fat) as control group, and the other DIO mice were fed with HFD, HFD with ROS (mixed 80 mg into 1 kg HFD) or HFD with compound A (mixed 2 g into 1 kg HFD) around 3 weeks. After 16 days of treatment, an IPGTT (I g/kg glucose) and an IPITT (0.75 U/kg insulin) were performed after 19 days as described above. After 21 days of dosing, we took blood from heart of anaesthetized fasted 10-hour mice. Tissues were collected and stored at −80° C.

Serum was used for all the analysis of blood parameters. We used Hitachi 7020 Automatic Analyzer (Hitachi, Tokyo, Japan) to measure serum triglyceride (TG), total cholesterol (TC), HDL cholesterol (HDL-c) and LDL cholesterol (LDL-c).

Experimental Results

After 3-week treatment, compounds A, B and C decreased serum triglyceride levels (TG) without affecting food intake and body weight of dio mice. Compared to the HFD mice group, compound A reduced the levels of TG around 23% o, and compounds B and C down-regulated the levels of serum TG by 20% and 12%, respectively. However, these three compounds did not significantly change serum cholesterol levels.

Figure 6:
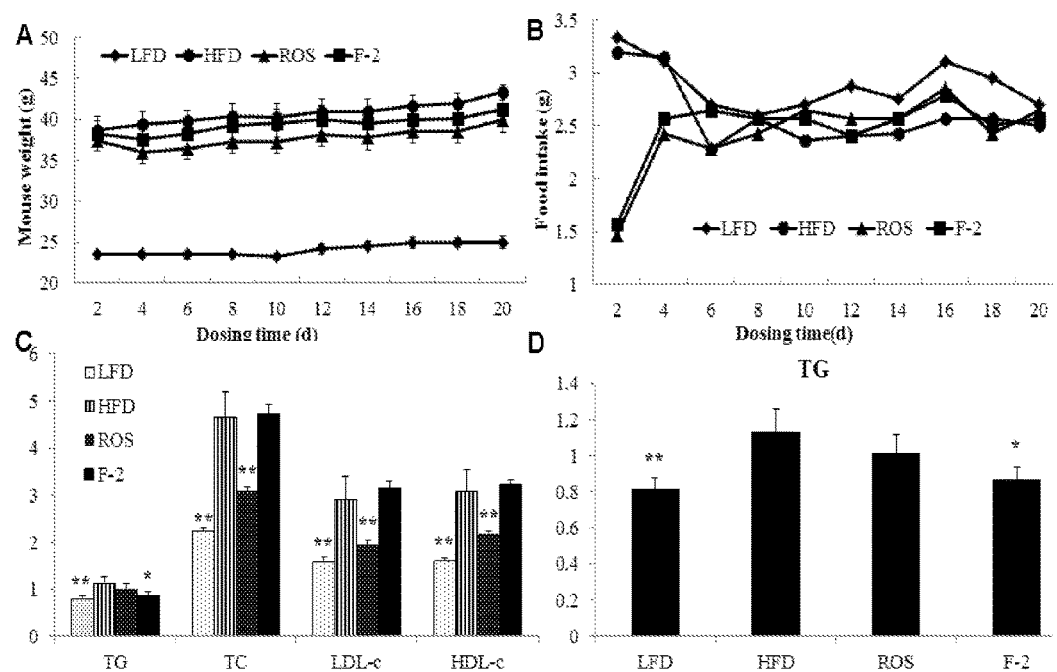
FIG. 6 shows the effects of bavachinin (compound A, labeled as F-2) on body weight, food intake and serum lipid parameters in dio mice.

FIG. 6 showed that the effects of compound A (F-2) on body weight, food intake and serum lipid parameters of dio mice. FIG. 6A showed that, compound A group did not increase mice body weight during the treatment compared with HFD groups; FIG. 6B exhibited compound A group did not affect food intake of mice during the treatment; FIG. 6C indicated that the effects of compound A on serum lipid parameters in dio mice; FIG. 6D showed compound A significantly reduced serum TG levels in contrast to HFD group.

In summary, the compounds of formula I according to the present invention can significantly increase transcriptional activities of PPAR α/γ and regulate the mRNA levels of their specific target genes involved in glucose and lipid catabolism. In addition, the animal results showed that the compounds of formula I treatment (100 mg/kg/d for 20 days) reduced glucose and triglycerides and improved intraperitoneal glucose tolerance (IPGTT) in db/db and diet-induced obese (dio) mice. Thus, the compounds of formula I can be used as potent dual PPAR α/γ agonist to prepare drugs and functional foods for preventing or/and treating metabolic syndrome, especially glucose or/and lipid disorders, with extensive and bright prospects of application.

Finally, it is necessary to illustrate: the above embodiments are only used for the further detailed descriptions for the technical solution of the present invention, can not be understood as the limit to the scope of the present invention, those unessential improvements and adjusts that are made by those skilled in the art according to the contents described above of the present invention are all belong to the scope of the present invention.

We claim:

1. A PPAR α/γ dual agonist for use in treating metabolic syndrome, comprising an amount of the compounds represented by formula I and/or its salts or solvates, wherein the formula I is:

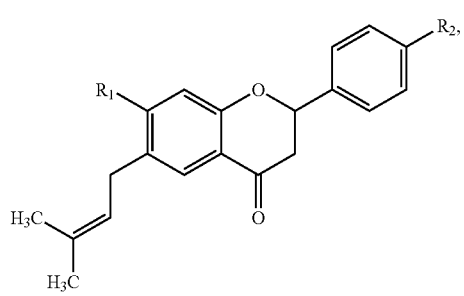

wherein:
R$_1$ is selected from C$_2$-C$_4$ alkoxyls;
R$_2$ is hydroxyl.

2. The PPAR α/γ dual agonist according to claim 1, wherein: R$_1$ is ethoxyl.

3. A PPAR α/γ dual agonist for use in treating metabolic syndrome, comprising an amount of the compounds represented by formula I and/or its salts or solvates, wherein the formula I is:

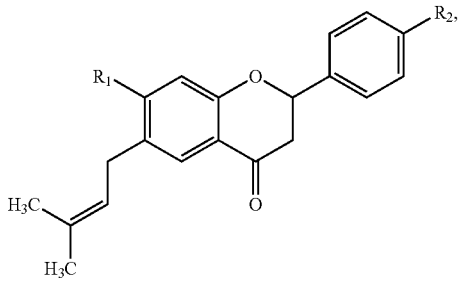

wherein: both R$_1$ and R$_2$ are methoxycarbonyl.

* * * * *